(12) United States Patent
Schaefer et al.

(10) Patent No.: US 7,897,699 B2
(45) Date of Patent: *Mar. 1, 2011

(54) SYNTHESIS OF PURIFIED, PARTIALLY ESTERIFIED POLYOL POLYESTER FATTY ACID COMPOSITIONS

(75) Inventors: Jared John Schaefer, Wyoming, OH (US); James Earl Trout, West Chester, OH (US)

(73) Assignee: The Procter & Gamble Company, Cincinnati, OH (US)

( * ) Notice: Subject to any disclaimer, the term of this patent is extended or adjusted under 35 U.S.C. 154(b) by 1149 days.

This patent is subject to a terminal disclaimer.

(21) Appl. No.: 10/935,505

(22) Filed: Sep. 7, 2004

(65) Prior Publication Data
US 2005/0042356 A1 Feb. 24, 2005

Related U.S. Application Data

(63) Continuation of application No. 10/156,476, filed on May 28, 2002, now Pat. No. 6,887,947.

(51) Int. Cl.
*C08G 63/00* (2006.01)
*C08F 281/00* (2006.01)

(52) U.S. Cl. ............... 525/437; 528/275; 528/295.3; 528/301; 528/406

(58) Field of Classification Search ............ 525/275, 525/295.3, 301, 437; 528/437, 275, 295.3, 528/301, 406
See application file for complete search history.

(56) References Cited

U.S. PATENT DOCUMENTS

| | | | |
|---|---|---|---|
| 3,823,145 A * | 7/1974 | Louvar | 544/401 |
| 4,611,055 A | 9/1986 | Yamamoto et al. | |
| 4,927,920 A | 5/1990 | Wagner et al. | |
| 4,954,621 A | 9/1990 | Masaoka et al. | |
| 4,983,731 A | 1/1991 | Wagner et al. | |
| 4,996,309 A | 2/1991 | Matsumoto et al. | |
| 5,580,966 A | 12/1996 | Buter et al. | |
| 5,648,483 A * | 7/1997 | Granberg et al. | 536/119 |
| 5,681,948 A | 10/1997 | Miller et al. | |
| 5,756,716 A | 5/1998 | Farone et al. | |
| 5,872,245 A | 2/1999 | Wilson | |
| 5,965,676 A * | 10/1999 | Anan et al. | 526/88 |
| 6,261,628 B1 | 7/2001 | Howie | |
| 6,504,003 B1 * | 1/2003 | Trout et al. | 528/271 |
| 6,887,947 B1 | 5/2005 | Schaefer et al. | |
| 6,900,310 B2 * | 5/2005 | Schaefer et al. | 536/124 |
| 7,304,153 B1 | 12/2007 | Appleby et al. | |
| 2002/0143137 A1 | 10/2002 | Howie et al. | |
| 2003/0228332 A1 | 12/2003 | Schaefer et al. | |
| 2003/0229224 A1 | 12/2003 | Schaefer et al. | |

FOREIGN PATENT DOCUMENTS

| | | |
|---|---|---|
| EP | 0 319 092 | 6/1989 |
| EP | 0 349 849 | 1/1990 |
| EP | 0 434 119 | 6/1991 |
| WO | WO 98/06731 | 2/1998 |
| WO | WO 99/48946 A2 | 9/1999 |
| WO | WO 99/49071 | 9/1999 |

OTHER PUBLICATIONS

"Handbook of Cosmetic Science and Technology", First Edition, 1993 Elsevier Science Publishers Ltd., Oxford OX2 7DH, UK, p. 28.
Herrington, Thelma M., et al., Phase Behavior of Some Sucrose Surfactants with Water and n-Decane, JAOCS, Oct. 1988, pp. 1677-1681, vol. 65, No. 10.

* cited by examiner

*Primary Examiner*—Milton I Cano
*Assistant Examiner*—Gennadiy Mesh
(74) *Attorney, Agent, or Firm*—Andrew J. Mueller; Stephen T. Murphy; Armina E. Matthews

(57) ABSTRACT

This invention relates to processes for the production of purified, partially esterified polyol fatty acid polyesters and the compositions derived from those processes. The purified, partially esterified polyol fatty acid polyesters of the present invention are particularly well suited for use in a variety of food, beverage, pharmaceutical, and cosmetic applications and comprise less than about 5% polyol; less than about 5 ppm of residual solvent; less than about 700 ppm of lower alky esters; less than about 5% of a soap and free fatty acid mixture; less than about 3% of ash; and have an acid value of less than about 6.

24 Claims, No Drawings

SYNTHESIS OF PURIFIED, PARTIALLY ESTERIFIED POLYOL POLYESTER FATTY ACID COMPOSITIONS

CROSS REFERENCE TO RELATED APPLICATION

This application is a continuation of U.S. application Ser. No. 10/156,476 filed May 28, 2002, now U.S. Pat. No. 6,887,947 issued on May 3, 2005.

BRIEF DESCRIPTION OF THE INVENTION

This invention relates to processes for the production of purified, partially esterified polyol fatty acid polyesters. More particularly, this invention relates to processes for preparing purified, partially esterified polyol fatty acid polyesters that include aqueous and alcohol based purification processes, and the products made according to those processes.

BACKGROUND OF THE INVENTION

As a result of their physical properties, partially esterified polyol fatty acid polyesters are commonly used as emulsifiers and surfactants in various food, beverage, and cosmetic compositions. There exists in the art various techniques for the synthesis of these partially esterified polyol fatty acid polyesters.

U.S. Pat. No. 4,927,920, to Wagner et al. discloses a process for the production of sugar esters with a degree of substitution of less than two by reacting a sugar, an organic solvent, and a sugar ester with a degree of substitution greater than two. The recovery of the solvent occurs at a temperature below the distillation temperature of the organic solvent.

U.S. Pat. No. 4,996,309, to Matsumoto et al. discloses a process for preparing sucrose fatty acid esters by reacting sucrose and fatty acid alkyl esters in the presence of a catalyst. The resulting sucrose esters are collected and washed with an acid solution.

Although conventional processes for the manufacture of partially esterified polyol fatty acid polyesters have known utilities, they suffer from several deficiencies, most notable of which are poor reaction control and the need for expensive, complex and continuous purification techniques. Additionally, these known processes are unable to accurately predict and consistently control the exact composition of the finished product without the use of complex sampling and control modification procedures throughout the reaction.

These known processes also suffer from an inability to accurately control the average degree of esterification in the final partially esterified polyol polyester compositions. Moreover, the partially esterified polyol polyester compositions produced from these known synthesis techniques typically contain unacceptable levels of impurities, such as solvent, polyol, lower alkyl esters, ash, soap, free fatty acids, and other unwanted reaction byproducts.

These limitations have heretofore constrained the industrial applicability and cost effective commercialization of these compounds in various food, beverage, pharmaceutical, and cosmetic applications.

Accordingly, it is an object of the present invention to provide processes for the synthesis of purified, partially esterified polyol polyesters that allow for the production of polyol polyesters with the degree of purity necessary for widespread incorporation into a variety of industrial and commercial applications. It is another object of the present invention to provide purified, partially esterified polyol polyester compositions with a degree of purity sufficient to be used in a variety of industrial and commercial applications. It is yet another object of the present invention to provide processes for the production of purified polyol polyesters that are efficient, cost effective, and require less purification than those now known and employed in the art.

SUMMARY OF THE INVENTION

This invention relates to processes for the production of purified, partially esterified polyol fatty acid polyesters and the compositions made from those processes. More particularly, this invention relates to processes for preparing partially esterified polyol fatty acid polyesters that include aqueous and alcohol based purification processes. The purified, partially esterified polyol fatty acid polyesters of the present invention are particularly well suited for use in a variety of food, beverage, pharmaceutical, and cosmetic applications, and comprise less than about 5% polyol; less than about 5 ppm of residual solvent; less than about 700 ppm of lower alky esters; less than about 5% of a soap and free fatty acid mixture; less than about 3% of ash; and an acid value of less than about 6. In a preferred embodiment of the present invention the purified partially esterified polyol polyester is a purified partially esterified sucrose polyester comprising less than about 4% sucrose; less than about 3 ppm of residual solvent; less than about 700 ppm of lower alky esters; less than about 5% of a soap and free fatty acid mixture; less than about 3% of ash; and an acid value of less than about 4.

DETAILED DESCRIPTION OF THE INVENTION

The present invention encompasses esterification processes for the production of partially esterified polyol fatty acid polyesters, in particular highly purified, partially esterified polyol fatty acid polyesters. The present invention will now be described in detail with reference to specific embodiments.

A. Definitions

Various publications and patents are referenced throughout this disclosure. All references cited herein are hereby incorporated by reference. Unless otherwise indicated, all percentages and ratios are calculated by weight. All percentages and ratios are calculated based on the total dry composition unless otherwise indicated.

All component or composition levels are in reference to the active level of that component or composition, and are exclusive of impurities, for example, residual solvents or by-products, which may be present in commercially available sources.

Referred to herein are trade names for components including various ingredients utilized in the present invention. The inventors herein do not intend to be limited by materials under a certain trade name. Equivalent materials (e.g., those obtained from a different source under a different name or catalog number) to those referenced by trade name may be substituted and utilized in the compositions, kits, and methods herein.

As used herein, and unless otherwise indicated, the use of a numeric range to indicate the value of a given variable is not intended to be limited to just discrete points within that stated range. One of ordinary skill in the art will appreciate that the use of a numeric range to indicate the value of a variable is meant to include not just the values bounding the stated range, but also all values and sub-ranges contained therein. By way of example, consider variable X that is disclosed as having a value in the range of A to B. One of ordinary skill in the art will understand that variable X is meant to include all integer and non-integer values bounded by the stated range of A to B. Moreover, one of ordinary skill in the art will appreciate that the value of the variable also includes all combinations and/or permutations of sub-ranges bounded by the integer and non-integer values within and including A and B.

As used herein, the term "partially esterified polyol polyester" is intended to include those esters of the polyol having a degree of esterification in excess of the degree of esterification of the polyol, but less than the degree of esterification of the highly esterified polyol fatty acid polyester. As used herein, the term "degree of esterification" refers to the average percentage of hydroxyl groups of a polyol composition that have been esterified.

In one embodiment of the present invention the polyol is sucrose having eight hydroxyl groups. The partially esterified sucrose polyester preferably has a degree of esterification of less than about 50%, preferably less than about 40%, more preferably less than about 30%, most preferably less than about 15%. As used herein the degree of esterification calculation does not include non-esterified polyol compounds that may be present.

In the description of the invention various embodiments and/or individual features are disclosed. As will be apparent to the ordinarily skilled practitioner, all combinations of such embodiments and features are possible and can result in preferred executions of the present invention.

B. Processes for Synthesizing Purified, Partially Esterified Polyol Polyester Fatty Acid Compositions In general, the processes for the preparation of purified, partially esterified polyol fatty acid polyesters of the present invention comprise the steps of forming an initial reaction product from an initial reaction mixture; forming a secondary reaction product by reacting the initial reaction product in the presence of a secondary reaction mixture; optionally neutralizing remaining catalyst; optionally forming a tertiary reaction product to recover reaction components (e.g., solvent) via such processes as evaporation; and purifying the tertiary reaction product and removing any isolated impurities and/or unreacted components.

i) Initial Reaction Product

An initial reaction product is formed by reacting an initial reaction mixture in an inert atmosphere, for a period of time in the range of from about 30 minutes to about 6 hours, and at a temperature in the range of from about 80° C. to about 140° C.

The initial reaction mixture comprises a polyol portion, a highly esterified polyol fatty acid polyester, a solvent, and a catalyst. Preferably, the molar ratio of the catalyst to the highly esterified polyol fatty acid polyester is in the range of from about 0.01:1 to about 10:1, more preferably in the range of from about 0.1:1 to about 5:1, yet more preferably from about 0.25:1 to about 1:1, most preferably in the range of from about 0.4:1 to about 0.6:1. Preferably the weight ratio of the solvent to the combined weight of the polyol portion, the highly esterified polyol ester fatty acid, and the catalyst is in the range of from about 1:1 to about 20:1, more preferably in the range of from about 3:1 to about 10:1, most preferably in the range of from about 4:1 to about 6:1. The molar ratio of polyol to highly esterified polyol polyester is in the range of from about 0.1:1 to about 40:1, preferably in the range of from about 1:1 to about 40:1, more preferably in the range of from about 5:1 to about 20:1, even more preferably in the range of from about 12:1 to about 18:1.

In one embodiment of the present invention the polyol is sucrose and the highly esterified polyol fatty acid polyester is sucrose polyester with a degree of esterification of about 95%.

As used herein, the term "polyol" is intended to include any aliphatic or aromatic compound containing at least two free hydroxyl groups. In practicing the processes disclosed herein, the selection of a suitable polyol is simply a matter of choice. For example, suitable polyols may be selected from the following classes: saturated and unsaturated straight and branched chain linear aliphatic; saturated and unsaturated cyclic aliphatic, including heterocyclic aliphatic; or mononuclear or polynuclear aromatics, including heterocyclic aromatics. Carbohydrates and glycols are exemplary polyols. Especially preferred glycols include glycerin. Monosaccharides suitable for use herein include, for example, mannose, galactose, arabinose, xylose, ribose, apiose, rhamnose, psicose, fructose, sorbose, tagitose, ribulose, xylulose, and erythrulose. Oligosaccharides suitable for use herein include, for example, maltose, kojibiose, nigerose, cellobiose, lactose, melibiose, gentiobiose, turanose, rutinose, trehalose, sucrose and raffinose. Polysaccharides suitable for use herein include, for example, amylose, glycogen, cellulose, chitin, inulin, agarose, zylans, mannan and galactans. Although sugar alcohols are not carbohydrates in a strict sense, the naturally occurring sugar alcohols are so closely related to the carbohydrates that they are also preferred for use herein. The sugar alcohols most widely distributed in nature and suitable for use herein are sorbitol, mannitol and galactitol.

Particular classes of materials suitable for use herein include monosaccharides, disaccharides and sugar alcohols. Other classes of materials include sugar ethers and alkoxylated polyols, such as polyethoxy glycerol.

In one embodiment of the present invention the polyol has on average at least four, preferably at least about 5, more preferably about 8 hydroxyl groups capable of being esterified per polyol molecule.

Suitable esterified epoxide-extended polyols include esterified propoxylated glycerols prepared by reacting a propoxylated glycerol having from 2 to 100 oxypropylene units per glycerol with $C_{10}$-$C_{24}$ fatty acids or with $C_{10}$-$C_{24}$ fatty acid esters, as described in U.S. Pat. Nos. 4,983,329 and 5,175,323, respectively, and esterified propoxylated glycerols prepared by reacting an epoxide and a triglyceride with an aliphatic polyalcohol, as described in U.S. Pat. No. 5,304,665 or with an alkali metal or alkaline earth salt of an aliphatic alcohol, as described in U.S. Pat. No. 5,399,728. Other polyols include acylated propylene oxide-extended glycerols having a propoxylation index of above about 2, preferably in the range of from about 2 to about 8, more preferably about 5 or above, wherein the acyl groups are $C_8$-$C_{24}$, preferably $C_{14}$-$C_{18}$, compounds, as described in U.S. Pat. Nos. 5,603,978 and 5,641,534 and fatty acid-esterified propoxylated glycerols, as described in U.S. Pat. Nos. 5,589,217 and 5,597,605.

Other suitable esterified epoxide-extended polyols include esterified alkoxylated polysaccharides. Preferred esterified alkoxylated polysaccharides are esterified alkoxylated polysaccharides containing anhydromonosaccharide units, more preferred are esterified propoxylated polysaccharides containing anhydromonosaccharide units, as described in U.S. Pat. No. 5,273,772.

The polyol has a degree of esterification less than the degree of esterification of both the partially esterified polyol polyester and the highly esterified polyol fatty acid polyester. The first polyol portion may be a single type or class of polyol (e.g., sucrose) or may alternatively be a blend of two or more types or classes of polyols (e.g., a sugar alcohols, such as sorbitol; monosaccharides, such as fructose; and oligosaccharides, such as maltose).

As used herein, the term "highly esterified polyol fatty acid polyester" is intended to include those esters of a polyol with a degree of esterification in excess of the degree of esterification of both the polyol and the partially esterified polyol polyester. In one embodiment of the invention the highly esterified polyol polyester has a degree of esterification of at least about 70%, while in yet another embodiment the highly esterified polyol polyester has a degree of esterification of at least about 90%, preferably at least about 95%.

A variety of processes are known in the art for the synthesis of highly esterified polyol fatty acid polyesters that are suitable for use in the processes of the present invention. Examples of such processes are detailed in U.S. Pat. No. 3,963,699, to Rizzi et al., disclosing a solvent-free transesterification process in which a mixture of a polyol (such as sucrose), a fatty acid lower alkyl ester (such as a fatty acid methyl ester), an alkali metal fatty acid soap, and a basic catalyst is heated to form a homogenous melt. Excess fatty acid lower alkyl ester is added to the melt to form the higher polyol fatty acid polyesters. The polyesters are then separated from the reaction mixture by any of the routinely used separation procedures; distillation or solvent extraction are preferred. Additional suitable processes include U.S. Pat. Nos. 4,517,360, to Volpenhein et al.; 5,422,131, to Elsen et al.; 5,648,483, to Granberg et al.; 5,767,257, to Schafermeyer et al., and 6,261,628, to Howie et al., each of which is herein incorporated by reference.

In one embodiment of the present invention, the highly esterified polyol fatty acid polyesters are sucrose fatty acid polyesters, having an average of at least 4 fatty acid groups per molecule. In another embodiment of the invention, the highly polyol fatty acid polyester is sucrose fatty acid polyester having an average of at least 5 fatty acid groups per molecule, while in another embodiment the sucrose fatty acid polyesters have an average of from about 5 to about 8 fatty acid groups per molecule. In yet another embodiment, the polyol polyester is a sucrose polyester wherein at least about 75% of the sucrose polyester comprises octaester.

The fatty acid chains of the highly esterified polyol fatty acid polyesters may be branched, linear, saturated, unsaturated, hydrogenated, unhydrogenated, or mixtures thereof. The fatty acid chains of the fatty acid esters have from about 6 to about 30 total carbon atoms. As used herein, reference to a fatty acid compound having fatty acid chains of a particular length is intended to mean that a majority of the fatty acid chains, i.e., greater than 50 mol % of the fatty acid chains, have the stated length. In a more specific embodiment, the fatty acid compounds have greater than about 60 mol %, and more specifically greater than about 75 mol %, of fatty acid chains of the stated length. As used herein "fatty acid ester" is intended to include fatty acid esters in which the fatty acid chains have a total of from about 2 to about 28, typically from about 8 to about 22, carbon atoms. The fatty acid esters may be branched, unbranched, saturated, unsaturated, hydrogenated, unhydrogenated, or mixtures thereof.

In one embodiment of the present invention, the fatty acid chains of the polyester may be branched or linear and may be formed from fatty acid esters having fatty acid chains of from about 8 to about 26 total carbon atoms. In yet another embodiment, the fatty acid chains of the fatty acid ester have from about 16 to about 22 total carbon atoms.

Other suitable polyol fatty acid polyesters are esterified linked alkoxylated glycerins, including those comprising polyether glycol linking segments, as described in U.S. Pat. No. 5,374,446 and those comprising polycarboxylate linking segments, as described in U.S. Pat. Nos. 5,427,815 and 5,516,544.

Additional suitable polyol fatty acid polyesters are esterified epoxide-extended polyols of the general formula $P(OH)_{A+C}(EPO)_N(FE)_B$ wherein P(OH) is a polyol, A is from 2 to about 8 primary hydroxyls, C is from about 0 to about 8 total secondary and tertiary hydroxyls, A+C is from about 3 to about 8, EPO is a $C_3$-$C_6$ epoxide, N is a minimum epoxylation index average number, FE is a fatty acid acyl moiety and B is an average number in the range of greater than 2 and no greater than A+C, as described in U.S. Pat. No. 4,861,613. The minimum epoxylation index average number has a value generally equal to or greater than A and is a number sufficient so that greater than 95% of the primary hydroxyls of the polyol are converted to secondary or tertiary hydroxyls. Preferably the fatty acid acyl moiety has a $C_7$-$C_{23}$ alkyl chain.

The highly esterified polyol fatty acid polyester may be comprised of a single type or class of polyol polyester (e.g., sucrose) or may alternatively be a blend of two or more types or classes of polyol polyesters (e.g., a sugar alcohols, such as sorbitol; monosaccharides, such as fructose; and oligosaccharides, such as maltose). The polyol backbones of the highly esterified polyol fatty acid polyesters (e.g., sucrose in a highly esterified sucrose fatty acid polyester) may be the same backbone as the polyol, or may optionally be comprised of two or more different polyol backbones.

In one embodiment of the present invention the polyol is sucrose and the highly esterified polyol fatty acid polyester is predominantly (i.e., in excess of about 95%, preferably in excess of about 98%, more preferably in excess of about 99%) comprised of sucrose fatty acid polyester. In another embodiment the polyol is glucose and the highly esterified polyol fatty acid polyester is sucrose fatty acid polyester. In yet another embodiment, the polyol is sucrose and the highly esterified fatty acid polyester is comprised of sucrose fatty acid polyester and a highly esterified epoxide-extended polyol polyester.

Suitable basic compounds to be used as basic reaction catalysts include alkali metals such as sodium, lithium and potassium; alloys of two or more alkali metals such as sodium-lithium and sodium-potassium alloys; alkali metal hydrides, such as sodium, lithium and potassium hydride; alkali metal lower ($C_1$-$C_4$) alkyls such as butyl-lithium; and alkaline metal alkoxides of lower ($C_1$-$C_4$) alcohols, such as lithium methoxide, potassium t-butoxide, potassium methoxide, and/or sodium methoxide. Other suitable basic compounds include carbonates and bicarbonates of alkali metals or alkaline earth metals. Preferred classes of basic catalysts include potassium carbonate, sodium carbonate, barium carbonate, or mixtures of these compounds having particle sizes that are less than about 100 microns, preferably less than about 50 microns. These preferred catalysts could be used in admixture with the more conventional basic catalysts, described above. Potassium carbonate and/or potassium methoxide are also preferred catalysts. These catalysts are further disclosed in U.S. Pat. No. 4,517,360, to Volpenhein et al., which is incorporated by reference.

Applicants have found that during the initial reaction phase it is preferable that the initial reaction mixture be as homogeneous as possible. A homogenous initial reaction mixture can be achieved by selection of appropriate reaction mixture ingredients that dissolve in the presence of the selected solvent. Examples of suitable solvents are selected from the group consisting of dimethyl formamide, acetonitrile, acetone, and mixtures thereof. Dimethyl formamide is a particularly preferred solvent.

If the preferred degree of homogeneity is not readily achieved upon the admixing of the initial reaction mixture components, either by virtue of the ingredients or various other processing parameters selected, a sufficient amount of agitation may be applied during the initial reaction phase to form an approximately homogeneous mixture or emulsion. Agitation should be applied for a period of time necessary to maintain homogeneity throughout the duration of the initial reaction. Once agitation has been applied for a period of time necessary to assure homogeneity of the reactants throughout the reaction, further application of agitation may be continued, discontinued, or varied in force.

As used herein the term, "a sufficient amount of agitation" is defined as the level of agitation necessary to ensure that reaction components (e.g., the initial reaction mixture) do not separate into discrete phases for a period of time in excess of about 10 seconds, preferably in excess of about 20 seconds, more preferably in excess of about 30 seconds, more preferably in excess of about 45 seconds, most preferably in excess of about 60 seconds, following discontinuation of the agitation. Preferably, agitation is applied during the reaction for a period of time sufficient to ensure that the degree of esterification of the highly esterified polyol polyester fatty acid is less than about 50%, preferably less than about 40%, more preferably less than about 30%, most preferably less than about 15%.

In one embodiment of the present invention a heterogeneous initial reaction mixture comprises sucrose, a highly esterified sucrose fatty acid with a degree of esterification of about 95%, a potassium carbonate catalyst, and dimethyl formamide (DMF) as a solvent. Agitation is applied by use of a rotating impeller. The degree of agitation necessary to ensure a suitable degree of homogeneity throughout the reaction is quantified by a Weber Number in the range of from about 2000 to about 20,000, operating for a period of time in the range of from about 10 minutes to about 6 hours. In another embodiment the degree of agitation necessary to ensure suitable homogeneity is quantified by a Weber Number of about 10,000, applied for approximately 60 minutes. In yet another embodiment the agitation is quantified by a Weber Number of about 9,000 applied for the entire duration of a 120-minute reaction time.

As used herein, any device capable of inducing motion in the fluid reaction mixtures over a range of viscosities, thus effecting a dispersion of the components, is a suitable agitator for use in the processes of the present invention. Examples of suitable agitators include, impellors, paddles, kneaders, helical rotors, single sigma blade, double sigma blades, screw-type agitators, ribbon agitators, and mixtures thereof.

As used herein, the "Weber Number" is a dimensionless number intended to provide a system independent measure of the agitation force applied to a reaction mixture. The Weber Number is defined by Equation 1.

$$\frac{(\text{Density of the Continuous Phase}) \times (RPM \text{ of the Impellor})^2 \times (\text{Diameter of the Impellor})^3}{\text{Interfacial Tension between the Continuous and Discontinuous Phases}} \quad \text{Equation 1.}$$

ii) Catalyst Neutralization

Optionally, any catalyst remaining subsequent to the formation of the initial reaction product may be neutralized with an acid. Applicants have hereby found that neutralization of the remaining catalyst reduces the risk of saponification and base catalyzed hydrolysis reactions during aqueous purification, both of which adversely impact the purity of the partially esterified polyol fatty acid compositions.

To effectively neutralize any residual catalyst, a sufficient amount of an acid is added to the initial reaction product such that the molar ratio of the acid to total catalyst is in the range of from about 0.01:1 to about 1:1, preferably in the range of from about 0.1:1 to about 0.8:1, more preferably in the range of from about 0.6:1 to about 0.8:1. Examples of acids suitable for use in neutralizing any residual base catalyst include those acids selected from the group consisting of hydrochloric, phosphoric, chromic, iodic, benzoic, hydrofluoric, sulfuric, sulfurous, acetic, formic, nitric, and mixtures thereof.

iv) Secondary Reaction Product

Optionally, a Secondary reaction product may be formed subsequent to the formation of the initial reaction product. The primary purpose for forming the secondary reaction product is to recover various initial reaction mixture components, such as solvent, that are no longer required for the remaining purification processes. Additionally, removal of the solvent by formation of the secondary reaction product reduces the amount of solvent present in the final partially esterified polyol fatty acid polyester compositions.

The secondary reaction product is formed by reacting the secondary reaction product at a pressure in the range of from about 0.01 mmHg to about 760 mmHg, preferably in the range of from about 0.1 mmHg to about 20 mmHg, more preferably in the range of from about 0.1 mmHg to about 10 mmHg, most preferably in the rang of from about 0.1 mmHg to abut 5 mmHg, and for a period of time in the range of from about 30 minutes to about 4 hours.

In one embodiment of the present invention the desired reaction pressure dictates the temperature at which the secondary reaction product is formed. In another embodiment of the invention the desired reaction temperature dictates the reaction pressure to be employed. Preferably the secondary reaction product is formed at the temperature-pressure combination at which distillation of the solvent used in the initial reaction mixture occurs.

In yet another embodiment the solvent is dimethyl formamide. Preferred temperature-pressure combinations for dimethyl formamide are selected from the group consisting of about 0.1 mmHg and about negative 21° C., about 1 mmHg and about 6° C., about 10 mmHg and about 41° C., about 100 mmHg and about 91° C., and about 760 mmHg and about 153° C.

One of ordinary skill in the art will appreciate upon reading the disclosure herein that the temperatures disclosed in the preferred temperature-pressure combinations refer to the temperature of the reaction ingredients, not the temperature setting of the equipment used to heat the reaction components. The ordinarily skilled artisan will also appreciate that the temperatures are approximations based on the distillation temperatures of the pure solvent and may vary slightly depending on the degree of solvent purity.

In one embodiment of the present invention, the step of neutralizing any remaining catalyst is performed subsequent to the formation of the initial reaction product, but prior to the formation of a secondary reaction product. In another embodiment the secondary reaction product is formed subsequent to the formation of the initial reaction product, though prior to the neutralization of remaining catalyst. In yet another embodiment, the remaining catalyst is neutralized with an acid without the formation of a secondary reaction product. In yet another embodiment the secondary reaction product is formed, while the remaining catalyst is not neutralized.

v) Purification (a) Solvent Free Aqueous Purification Processes

The reaction products of the present invention may be purified by an aqueous purification process, via application of a water washing solution. Applicants have found that in order to obtain partially esterified polyol polyester compositions with the requisite degree of purity, the aqueous purification process should be free of any solvents that would adversely affect the finished product purity requirement for the composition's intended use (e.g., food grade purity). As any solvent added after formation of the initial reaction product must ultimately be removed via a purification process, it is particularly preferred that the aqueous purification process be a solvent free purification process.

The water washing solution comprises from about 0.1% to about 5% of a salt and from about 95% to about 99.9% water. The water washing solution is applied over a period of time in the range of from about 2 minutes to about 30 minutes, preferably in the rang of from about 5-10 minutes. The weight ratio of the water washing solution to the initial weight of the reaction product to be purified (e.g., initial reaction product; secondary reaction product; acid neutralized initial reaction product; or acid neutralized secondary reaction product) is in the range of from about 3:1 to about 30:1, preferably in the range of from about 5:1 to about 20:1, more preferably in the range of from about 8:1 to about 15:1. The temperature of the water washing solution is in the range of from about 20° C. to about 100° C., and the temperature of the reaction product to be purified is in the range of from about 20° C. to about 100° C. Preferably the temperature of the water washing solution is in the range of from about 20° C. to about 60° C. when the majority of the fatty acid esters are unsaturated, and in the range of from about 40° C. to about 80° C. when the majority of the fatty acid esters are saturated.

Examples of salts suitable for use in the present invention include salts selected from the group consisting of calcium salts, magnesium salts, barium salts, sodium salts, potassium salts, cesium salts, and mixtures thereof. Preferred salts for use in the present invention include salts selected from the group consisting of lithium chloride, lithium bromide, lithium iodide, lithium sulfate, calcium chloride, calcium bromide, calcium iodide, calcium sulfate, magnesium chloride, magnesium bromide, magnesium iodide, magnesium sulfate, barium chloride, barium bromide, barium iodide, barium sulfate, sodium chloride, sodium bromide, sodium iodide, sodium sulfate, potassium chloride, potassium bromide, potassium iodide, potassium sulfate, cesium chloride, cesium bromide, cesium iodide, cesium sulfate, and mixtures thereof. Salts selected from the group consisting of calcium chloride, calcium bromide, calcium iodide, calcium sulfate, and mixtures thereof are particularly preferred.

Preferably, the water portion of the water washing solution is mixed with the reaction product to be purified for a period of time in the range of from about 2 minutes to about 15 minutes prior to the introduction of the salt. Subsequently, the salt is added to the water/reaction product combination and mixed for an additional period of time in the range of from about 2 minutes to about 15 minutes. Not to be limited by theory, Applicants believe that the salt facilitates the separation of impurities and other unwanted reaction byproducts from the finished product composition.

Following application of the water washing solution, impurities, unreacted components, and reaction byproducts are collected and removed from the washed reaction product. The washed reaction product separates into two discrete layers. The top layer contains the impurities, solvent, reaction byproducts, and unreacted reaction components to be removed and discarded. The bottom layer contains the partially esterified polyol fatty acid polyester. Optionally, the top layer may be collected and processed to recover and/or recycle any desired reaction ingredients and/or byproducts (e.g., polyol and solvent).

Separation into the discrete phases may be accomplished by allowing the washed reaction products to gravity settle. Preferred methods for the separation and isolation of impurities include centrifugation for a period of time in the range of from about 5 minutes to about 30 minutes at an applied force of from about 100 G to about 15000 G. Alternatively, when the majority (i.e., in excess of about 50%) of the fatty acid esters of the reaction product to be purified (e.g., initial reaction product; secondary reaction product; acid neutralized initial reaction product; or acid neutralized secondary reaction product) comprise unsaturated fatty acid esters, separation into discrete phases may be achieved via temperature reduction. The temperature separation step, wherein the temperature of the washed reaction product is decreased to a temperature below about 20° C., preferably below about 15° C., more preferably below about 10° C., more preferably below about 5° C., most preferably at or below about 0° C., occurs after washing with a solvent free aqueous wash solution. As the temperature decreases, the washed reaction product separates into two discrete layers, an upper layer containing impurities and a bottom layer comprising purified reaction product. The upper layer containing the impurities is collected and removed. The bottom layer comprising purified, partially esterified polyol fatty acid polyesters can be either collected for final processing or subjected to additional purification processes.

The various techniques for the isolation and removal of impurities and unwanted reaction byproducts described herein may be used either independently or in combination. In one embodiment of the present invention isolation of impurities occurs by centrifugation. In another embodiment, isolation is achieved by employing both centrifugation and temperature reduction processes. In yet another embodiment, a product purification cycle comprising the steps of washing the reaction product with a solvent free water washing solution and then centrifuging the washed reaction product to isolate impurities is repeated for a total of ten times. Subsequent to the tenth washing-centrifuging cycle, the temperature of the washed reaction product is decreased to about 0° C. As the temperature approaches 0° C. the washed reaction product separates into two discrete layers. The top layer containing the impurities is isolated and removed, and the bottom layer comprising the purified reaction product is collected for final processing.

The purification process of washing the reaction product and separating and collecting the partially esterified polyol polyester may optionally be performed one or more additional times, depending on product composition at the end of the purification cycle and the desired finished product purity specification. Preferably the purification cycle is repeated in the range of from about 1 to about 20 times to achieve particularly high degrees of purification.

In one embodiment of the present invention the water washing purification steps are repeated in the range of from about 5 to about 15 times. The quantity of water washing solution to be used in each purification cycle is calculated based on the initial weight of the reaction product to be purified (i.e., the weight of the reaction product prior to the first purification cycle). In each cycle the weight ratio of the water washing solution to the initial weight of the washed reaction product to be purified (e.g., initial reaction product; secondary reaction product; acid neutralized initial reaction product; or acid neutralized secondary reaction product) is within the range of from about 3:1 to about 30:1, preferably in the range of from about 5:1 to about 20:1, more preferably in the range of from about 8:1 to about 15:1.

The quantity of water washing solution utilized may be substantially the same for each purification cycle, or alternatively may vary from cycle to cycle. Additionally, the quantity of salt utilized in the water wash solution may be substantially the same for each purification cycle, or alternatively may vary from cycle to cycle. Combinations of varying amounts of water and salt within the water washing solution of various purification cycles are also contemplated.

In one embodiment, the quantity of salt utilized in the water washing solutions of a purification cycle subsequent to the first purification cycle is less than the quantity of salt utilized in the first purification cycle.

For each of the purification cycles the temperature of the water washing solution is in the range of from about 20° C. to about 100° C., and the temperature of the reaction product to be purified is in the range of from about 20° C. to about 100° C.

Optionally, the weight ratio of water washing solution to reaction product to be purified may be recalculated after each purification cycle, such that the weight ratio of the water washing solution to the weight of the reaction product to be purified in a given purification cycle is in the range of from about 3:1 to about 30:1, preferably in the range of from about 5:1 to about 20:1, more preferably in the range of from about 5:1 to about 10:1.

When the majority (i.e., in excess of about 50%) of fatty acid esters of the reaction product to be purified (e.g., initial reaction product; secondary reaction product; acid neutralized initial reaction product; or acid neutralized secondary reaction product) comprise unsaturated fatty acid esters, the last phase of the purification cycle may optionally contain a freezing step. The freezing step occurs after the final aqueous wash and centrifugation.

Following the final wash with the water washing solution, the top layer containing the impurities and other unwanted reaction byproducts is collected and removed. The temperature of the bottom layer comprising the purified reaction product is then lowered to a temperature at or below about 0° C. As the temperature decreases, the bottom layer separates into two discrete layers, an upper layer which contains impurities, and a bottom layer comprising further purified reaction product. The upper layer containing the impurities is collected and discarded, leaving a purified reaction product comprising partially esterified polyol fatty acid polyesters.

(b) Alcohol Purification Processes

The reaction products of the present invention may optionally be purified by an alcohol purification process, via application of an alcohol washing solution. Applicants have found that in order to obtain partially esterified polyol polyester compositions with the requisite degree of purity, the alcohol purification process should be free of any additional solvents that would adversely affect the finished product purity requirement for the composition's intended use (e.g., food grade purity). As any solvent added after formation of the initial reaction product must ultimately be removed via a purification process, it is preferred that the alcohol washing solution contain no additional ingredients that would not be substantially removed, preferably completely removed, by the alcohol wash process. Particularly preferred embodiments of the resent invention are those where the alcohol wash solution comprises no ingredients, other than perhaps impurities at a level that would not adversely impact finished product purity, beyond the alcohol.

The alcohol washing solution comprises alcohols with a carbon chain length in the range of from about 2 atoms to about 5 atoms. The alcohol washing solution is applied over a period of time in the range of from about 2 minutes to about 30 minutes, preferably in the rang of from about 5-10 minutes. The weight ratio of the alcohol washing solution to the initial weight of the reaction product to be purified (e.g., initial reaction product; secondary reaction product; acid neutralized initial reaction product; or acid neutralized secondary reaction product) is in the range of from about 3:1 to about 30:1, preferably in the range of from about 5:1 to about 20:1, more preferably in the range of from about 5:1 to about 10:1.

The temperature of the alcohol washing solution is in the range of from about 20° C. to about 100° C., and the temperature of the reaction product to be purified is in the range of from about 20° C. to about 100° C. Preferably the temperature of the alcohol washing solution is in the range of from about 20° C. to about 60° C. when the majority of the fatty acid esters are unsaturated, and in the range of from about 40° C. to about 80° C. when the majority of the fatty acid esters are saturated.

Examples of alcohols suitable for use in the present invention include ethanol, n-propanol, n-butanol, n-pentanol, branched and non-terminal forms of $C_2$-$C_5$ alcohols, and mixtures thereof. Preferred alcohols are selected from the group consisting of ethanol, n-propanol, n-butanol, n-pentanol, and mixtures thereof.

Following application of the alcohol washing solution, impurities, unreacted components, and reaction byproducts are collected and removed from the washed reaction product. The washed reaction product separates into two discrete layers. The bottom layer contains the impurities, solvent, reaction byproducts, and unreacted reaction components to be removed and discarded. The top layer contains the partially esterified polyol fatty acid polyester. Optionally, the bottom layer may be collected and processed to recover and/or recycle any desired reaction ingredients and/or byproducts (e.g., polyol and solvent).

Separation into the discrete phases may be accomplished by allowing the impurities and byproducts to gravity settle. Preferred methods for the separation and isolation of impurities include centrifugation for a period of time in the range of from about 5 minutes to about 30 minutes at an applied force of from about 100 G to about 15000 G, preferably in the range of from about 2,000 G to about 10,000 G.

The purification cycle of washing the reaction product with alcohol and separating and collecting the partially esterified polyol polyester may optionally be performed one or more additional times, depending on the product composition following the purification cycle and the desired degree of purity in the finished product. Preferably the purification process is repeated in the range of from about 1 to about 20 times to achieve particularly high degrees of purification.

In one embodiment of the present invention the alcohol washing purification steps are repeated in the range of from about 5 to about 15 times. The quantity of alcohol washing solution to be used in each purification cycle is calculated based on the initial weight of the reaction product to be purified (i.e., the weight of the reaction product prior to the first purification cycle). In each cycle the weight ratio of the alcohol washing solution to the initial weight of the washed reaction product to be purified (e.g., initial reaction product; secondary reaction product; acid neutralized initial reaction product; or acid neutralized secondary reaction product) is within the range of from about 3:1 to about 30:1, preferably in the range of from about 5:1 to about 20:1, more preferably in the range of from about 8:1 to about 15:1. The quantity of alcohol washing solution utilized may be substantially the same for each purification cycle, or alternatively may vary from cycle to cycle.

For each of the purification cycles the temperature of the alcohol washing solution is in the range of from about 20° C. to about 100° C., and the temperature of the reaction product to be purified is in the range of from about 20° C. to about 100° C.

Optionally, the weight ratio of alcohol washing solution to reaction product to be purified may be recalculated after each purification cycle, such that the weight ratio of the alcohol washing solution to the weight of the reaction product to be purified in a given purification cycle is in the range of from about 3:1 to about 30:1, preferably in the range of from about 5:1 to about 20:1, more preferably in the range of from about 5:1 to about 10:1.

C. Composition of Purified, Partially-Esterified Polyol Fatty Acid Polyesters The purified, partially esterified polyol polyester fatty acid compositions of the present invention generally comprise a partially esterified polyol polyester with a degree of esterification of less than about 50%, preferably less than about 40%, more preferably less than about 30%, more preferably less than about 15%. Additionally, the purified, partially esterified polyol polyester fatty acid compositions comprise less than about 5% polyol, preferably less than about 3.5% polyol, more preferably less than about 2% polyol, more preferably less than about 1.1% polyol; less than about 5 ppm (parts per million) of residual solvent, preferably less than about 4 ppm of residual solvent, most preferably less than about 3 ppm of residual solvent; and less than about 700 ppm of lower alkyl esters, preferably less than about 650 ppm of lower alkyl esters, more preferably less than about 500 ppm of lower alkyl esters, more preferably less than about 200 ppm of lower alkyl esters, more preferably less than about 100 ppm of lower alkyl esters, most preferably less than about 50 ppm of lower alkyl esters of lower alkyl esters. Moreover, the purified, partially esterified polyol polyester compositions comprise less than about 5% of a soap and free fatty acid mixture, preferably less than about 4.5% of a soap and free fatty acid mixture, more preferably less than about 4% of a soap and free fatty acid mixture, more preferably less than about 3.5% of a soap and free fatty acid mixture, most preferably less than about 3.3% of a soap and free fatty acid mixture.

The purified, partially esterified polyol polyesters also comprise less than about 3% ash, preferably less than about 2% ash, more preferably less than about 1.7% ash. As used herein, the term "ash" refers to sulfated ash. The amount of sulfated ash in the present invention is calculated by weighing 5 grams of a sample into a platinum dish. Then 5 mL of 10% Sulfuric acid ($H_2SO_4$) is added to the sample, and the mixture is heated until carbonized. The carbonized ash is then baked in a muffle furnace at 550° C. until ashed. An additional aliquot of 2-3 mL of 10% Sulfuric Acid is added, and the mixture is again heated until carbonized. Again the mixture is baked at 550° C. until ashed. This process is repeated until the ash maintains a constant weight. The percentage of sulfated ash is calculated by dividing the weight of the remaining ash by the sample weight.

Furthermore, the purified polyester compositions of the present invention have an acid value of less than about 6, preferably an acid value less than about 4, more preferably an acid value less than about 3, most preferably an acid value less than about 2.

Not to be limited by theory, Applicants believe residual levels of lower alkyl ester impurities may be attributed to those amounts that exist as an impurity within the highly esterified polyol polyester fatty acids prior to inclusion in the initial reaction mixture. Soap and free fatty acid mixtures are believed to be byproducts resulting from polyol degradation and catalyst neutralization reactions. Ash is also believed to be a byproduct of various degradation and purification processes within the synthesis of the purified, partially esterified polyol polyester compositions.

D. Examples

The following are non-limiting examples of partially esterified polyol polyester and purified, partially esterified polyol polyester compositions and methods of making the same, used in accordance with the present invention. The following examples are provided to illustrate the invention and are not intended to limit the spirit or scope thereof in any manner.

Example 1

In the present example, an initial reaction mixture comprises 75 g (0.0314 moles) of sucrose polyester, based on oleic fatty acids, with a degree of esterification of 96%; 161 g (0.471 moles) of sucrose; 7 g (0.0507 moles) of potassium carbonate; and 530 g of dimethyl formamide solvent. Prior to use in the initial reaction mixture the sucrose and catalyst were dried in a vacuum oven for 12 hours. An initial reaction product is formed by reacting the initial reaction mixture at 100° C. for 300 minutes in a two-piece, baffled glass reactor. The initial reaction mixture is reacted in the presence of agitation to ensure even heat distribution of the reaction components.

A sample of the initial reaction product is analyzed by super fluid chromatography (SFC) and found to have the composition shown in Table 1A, wherein $SE_X$ indicates a Sucrose Ester with X esterified hydroxyl groups. Suitable super fluid chromatography analytical methods are described in co-pending application U.S. patent Ser. No. 09/646,293, filed Sep. 15, 2000 to Trout et al., entitled Improved Processes for Synthesis and Purification of Nondigestible Fats.

TABLE 1A

| Soap | Sucrose | $SE_1$ | $SE_2$ | $SE_3$ | $SE_4$ | $SE_5$ | $SE_6$ | $SE_7$ | $SE_8$ |
|---|---|---|---|---|---|---|---|---|---|
| 1.0 | 45.4 | 38.1 | 13.4 | 2.2 | 0.0 | 0.0 | 0.0 | 0.0 | 0.0 |

Example 2

In the present example, an initial reaction mixture comprises 75 g (0.0314 moles) of sucrose polyester with a degree of esterification of 96%; 161 g (0.471 moles) of sucrose; 5 g (0.036 moles) of potassium carbonate; and 540 g of dimethyl formamide solvent. An initial reaction product is formed by reacting the initial reaction mixture at 100° C. for 300 minutes in a two-piece, baffled glass reactor. The initial reaction mixture is reacted in the presence of agitation to ensure even heat distribution of the reaction components.

A sample of the initial reaction product is analyzed by Super Fluid Chromatography (SFC) and found to have the composition shown in Table 2A.

TABLE 2A

| Soap | Sucrose | $SE_1$ | $SE_2$ | $SE_3$ | $SE_4$ | $SE_5$ | $SE_6$ | $SE_7$ | $SE_8$ |
|---|---|---|---|---|---|---|---|---|---|
| 1.0 | 45.2 | 38.2 | 13.5 | 2.2 | 0.0 | 0.0 | 0.0 | 0.0 | 0.0 |

The initial reaction product weighs 781 g. 736 g of the initial reaction product is then evaporated in a round bottom flask heated in a 60° C. water bath, under a pressure of 0.8 mmHg, for 120 minutes to form a secondary reaction product. The secondary reaction product weighs 270 g.

A sample of the secondary reaction product is analyzed by Supercritical Fluid Chromatography (SFC) and found to have the composition shown in Table 2B.

TABLE 2B

| Soap | Sucrose | $SE_1$ | $SE_2$ | $SE_3$ | $SE_4$ | $SE_5$ | $SE_6$ | $SE_7$ | $SE_8$ |
|---|---|---|---|---|---|---|---|---|---|
| 1.1 | 44.6 | 36.9 | 14.1 | 3.1 | 0.0 | 0.0 | 0.0 | 0.0 | 0.0 |

Example 3

In the present example, an initial reaction mixture comprises 75 g (0.0314 moles) of sucrose polyester with a degree of esterification of 96%; 161 g (0.471 moles) of sucrose; 5 g (0.036 moles) of potassium carbonate; and 540 g of dimethyl formamide solvent. An initial reaction product is formed by reacting the initial reaction mixture in the presence of agitation at 100° C. for 300 minutes in a two-piece, baffled glass reactor.

A sample of the initial reaction product is analyzed by Super Fluid Chromatography (SFC) and found to have the composition shown in Table 3A.

TABLE 3A

| Soap | Sucrose | $SE_1$ | $SE_2$ | $SE_3$ | $SE_4$ | $SE_5$ | $SE_6$ | $SE_7$ | $SE_8$ |
|---|---|---|---|---|---|---|---|---|---|
| 1.1 | 45.4 | 38.0 | 13.4 | 2.2 | 0.0 | 0.0 | 0.0 | 0.0 | 0.0 |

The primary reaction product weighs 781 g and is treated with 2.5 g of 36.5% hydrochloric acid (0.025 moles) to neutralize the remaining catalyst. The initial reaction product is then evaporated in a round bottom flask heated in a 60° C. water bath, under a pressure of 0.6 mmHg, for 120 minutes to form a secondary reaction product. The secondary reaction product weighs 281 g.

210 g of the acid neutralized secondary reaction product is mixed in a stainless steel mixing vessel with 2100 g of 30° C. water for 5 minutes. The temperature is held constant. 5.25 g of calcium chloride is added to the system and mixed for an additional 5 minutes. The resulting mixture is centrifuged at 5000 G for 10 minutes. The centrifuged mixture splits into two discrete layers. The top layer is discarded and the bottom layer is recovered.

The entire bottom layer is collected and re-washed with 2100 g of 30° C. water for 5 minutes, holding the temperature constant. 5.25 g of calcium chloride are added and the system is mixed for an additional 5 minutes. The mixture is centrifuged at 5000 G for 10 minutes and the bottom layer is again recovered for further washing. The recovery and rewashing of the bottom layer is repeated for a total of three additional times, for a total of 5 washes with 5.25 g of calcium chloride.

After the fifth wash, the bottom layer is collected and re-washed in a stainless steel mixing vessel with 2100 g of 30° C. water for 5 minutes, holding the temperature constant. 3.15 g of calcium chloride are added, and the system is mixed for an additional 5 minutes. The mixture is centrifuged at 5000 G for 10 minutes and the bottom layer is again recovered for further washing. The process of collecting the bottom layer, rewashing in the presence of 3.15 g of calcium chloride, and centrifuging is repeated for a total of three additional times.

After the ninth total wash, the bottom layer is recovered and put into a freezer at −5° C. The bottom layer splits into two discrete phases. The top layer is discarded and the bottom layer is recovered and dried in a vacuum oven at 45° C. and 1 mmHg for 12 hours to produce a purified, partially esterified polyol fatty acid polyester composition.

The final product composition is analyzed by SFC and shown in Table 3B.

TABLE 3B

| DMF | Soap/FFA | Sucrose | Sulfated Ash | Acid Value | $SE_1$ | $SE_2$ | $SE_3$ | $SE_4$ | $SE_5$ | $SE_6$ | $SE_7$ | $SE_8$ |
|---|---|---|---|---|---|---|---|---|---|---|---|---|
| 1 ppm | 2.4 | 0.0 | 1.8% | 2.0 | 50.1 | 28.3 | 16.1 | 3.0 | 0.0 | 0.0 | 0.0 | 0.0 |

Example 4

In the present example, an initial reaction mixture comprises 77.5 g (0.0322 moles) of sucrose polyester having a degree of esterification of 96%; 200 g (0.585 moles) of sucrose; 2.0 g (0.0145 moles) of potassium carbonate; and 507 g of dimethyl formamide solvent. Prior to use in the initial reaction mixture the sucrose and catalyst were dried in a vacuum oven for 12 hours. An initial reaction product is formed by reacting the initial reaction mixture, in the presence of agitation, at 110° C. for 300 minutes in a two-piece, baffled glass reactor.

A sample of the initial reaction product is analyzed by Super Fluid Chromatography (SFC) and found to have the composition of Table 4A.

TABLE 4A

| Soap | Sucrose | $SE_1$ | $SE_2$ | $SE_3$ | $SE_4$ | $SE_5$ | $SE_6$ | $SE_7$ | $SE_8$ |
|---|---|---|---|---|---|---|---|---|---|
| 1.0 | 53.0 | 31.5 | 12.1 | 2.4 | 0.0 | 0.0 | 0.0 | 0.0 | 0.0 |

The initial reaction product weighs 751 g and is treated with 1.45 g of 36.5% hydrochloric acid (0.0141 moles) to neutralize the remaining catalyst. The mixture is then evaporated in a round bottom flask heated in a 60° C. water bath, under a pressure of 0.5 mmHg, for 120 minutes to form a secondary reaction product. The secondary reaction product weighs 339 g.

210 g of the secondary reaction product is mixed in a stainless steel mixing vessel with 2100 g of 30° C. water for 5 minutes. The temperature is held constant. 5.25 g of calcium chloride is added to the system and mixed for an additional 5 minutes. The resulting mixture is centrifuged at 5000 G for 10 minutes. The centrifuged mixture splits into two discrete layers. The top layer is discarded and the bottom layer is recovered.

The entire bottom layer is collected and re-washed with 2100 g of 60° C. water for 5 minutes, holding the temperature constant. 5.25 g of calcium chloride are added and the system is mixed for an additional 5 minutes. The mixture is centrifuged at 5000 G for 10 minutes and the bottom layer is again recovered for further washing. The recovery and rewashing of the bottom layer is repeated for a total of three additional times, for a total of 5 washes with 5.25 g of calcium chloride.

After the fifth wash, the bottom layer is collected and re-washed in a stainless steel mixing vessel with 2100 g of 60° C. water for 5 minutes, holding the temperature constant. 3.15 g of calcium chloride are added, and the system is mixed for an additional 5 minutes. The mixture is centrifuged at 5000 G for 10 minutes and the bottom layer is again recovered for further washing. The process of collecting the bottom layer, rewashing in the presence of 3.15 g of calcium chloride, and centrifuging is repeated for a total of three additional times.

After the ninth total wash, the bottom layer is recovered and put into a freezer at −5° C. The bottom layer splits into two discrete phases. The top layer is discarded and the bottom layer is recovered and dried in a vacuum oven at 45° C. and 1 mmHg for 12 hours to produce a purified, partially esterified polyol fatty acid polyester composition.

The final product composition is analyzed by SFC and shown in Table 4B.

TABLE 4B

| DMF | Soap/FFA | Sucrose | Sulfated Ash | Acid Value | $SE_1$ | $SE_2$ | $SE_3$ | $SE_4$ | $SE_5$ | $SE_6$ | $SE_7$ | $SE_8$ |
|---|---|---|---|---|---|---|---|---|---|---|---|---|
| 0.6 ppm | 2.0 | 0.0 | 1.7% | 2.7 | 61.2 | 29.2 | 7.6 | 0.0 | 0.0 | 0.0 | 0.0 | 0.0 |

Having now described several embodiments of the present invention it should be clear to those skilled in the art that the forgoing is illustrative only and not limiting, having been presented only by way of exemplification. Numerous other embodiments and modifications are contemplated as falling within the scope of the present invention as defined by the appended claims thereto.

What is claimed is:

1. A process for the preparation of a purified partially esterified polyol fatty acid polyester composition comprising the steps of:
   a) forming an initial reaction mixture, said initial reaction mixture comprising:
      i) a polyol portion;
      ii) a highly esterified polyol fatty acid polyester, said highly esterified polyester having a degree of esterification of at least about 80%;
      iii) a solvent; and,
      iv) a catalyst,
      wherein the molar ratio of said polyol portion to said highly esterified polyol polyester is in the range of from about 5:1 to about 40:1; wherein the molar ratio of said catalyst to said highly esterified polyol polyester is in the range of from about 0.01:1 to about 10:1, and wherein the weight ratio of said solvent to the combined weight of said polyol portion, said highly esterified polyol polyester, and said catalyst is in the range of from about 1:1 to about 20:1;
   b) forming an initial reaction product by reacting said initial reaction mixture in an inert atmosphere, in the presence of a sufficient amount of agitation, for a period of time in the range of from about 30 minutes to about 6 hours, and at a temperature in the range of from about 80° C. to about 140° C.; and
   c) optionally drying said initial reaction product,
   wherein the purified partially esterified polyol fatty acid polyester has a degree of esterification of less than about 40%.

2. The process of claim 1 wherein said polyol portion is sucrose, said highly esterified polyol polyester is highly esterified sucrose fatty acid polyester with a degree of esterification in excess of about 80%, and wherein said catalyst is selected from the group consisting of sodium, lithium, potassium, sodium-lithium alloys, sodium-potassium alloys, sodium hydride, lithium hydride, potassium hydride, butyl-lithium, lithium methoxide, potassium t-butoxide, potassium methoxide, sodium methoxide, potassium carbonate, sodium carbonate, barium carbonate, and mixtures thereof, and wherein said solvent is are selected from the group consisting of dimethyl formamide, acetonitrile, acetone, and mixtures thereof.

3. The process of claim 2, wherein in Step (b) agitation is applied at a Weber Number in the range of from about 5000 to about 15000, and for a period of time in the range of from about 30 minutes to about 6 hours.

4. The process of claim 3 wherein said highly esterified polyol polyester is highly esterified sucrose fatty acid polyester with a degree of esterification in excess of about 95%, said catalyst is selected from the group consisting of potassium carbonate, sodium carbonate, barium carbonate, and mixtures thereof; and wherein said solvent is dimethyl formamide.

5. A process for the preparation of a purified partially esterified polyol fatty acid polyester composition comprising the steps of:
   a) forming an initial reaction mixture, said initial reaction mixture comprising:
      i) a polyol portion;
      ii) a highly esterified polyol fatty acid polyester;
      iii) a solvent; and,
      iv) a catalyst,
      wherein the molar ratio of said polyol portion to said highly esterified polyol polyester is in the range of from about 5:1 to about 40:1; wherein the molar ratio of said catalyst to said highly esterified polyol polyester is in the range of from about 0.01:1 to about 10:1, and wherein the weight ratio of said solvent to the combined weight of said polyol portion, said highly esterified polyol polyester, and said catalyst is in the range of from about 1:1 to about 20:1;

b) forming an initial reaction product by reacting said initial reaction mixture in an inert atmosphere, in the presence of a sufficient amount of agitation, for a period of time in the range of from about 30 minutes to about 6 hours, and at a temperature in the range of from about 80° C. to about 140° C.;

c) adding an acid to the initial reaction product to neutralize any remaining catalyst, wherein the molar ratio of said acid to said catalyst is in the range of from about 0.01:1 to about 1:1;

d) forming a secondary reaction product by reacting said initial reaction product at a temperature-pressure combination at which distillation of said solvent occurs, wherein the pressure is in the range of from about 0.01 mmHg to about 760 mmHg, for a period of time in the range of from about 30 minutes to about 4 hours;

e) forming a purified reaction product by washing said secondary reaction product with a solvent free water washing solution, said solvent free water washing solution comprising:
(i) from about 0.1% to about 5% of a salt; and
(ii) from about 95% to about 99.9% water;
wherein the weight ratio of said water washing solution to said secondary reaction product is in the range of from about 3:1 to about 30:1, and wherein the temperature of said secondary reaction product and said water wash solution are in the range of from about 20° C. to about 100° C., wherein said wash time is in the range of from about 5 minutes to about 30 minutes;

f) isolating and removing impurities from said purified reaction product;

g) optionally repeating steps (e) and (f) for a number of times in the range of from about 1 to about 20; and, h) optionally drying said purification reaction product, wherein the purified partially esterified polyol fatty acid polyester has a degree of esterification of less than about 40%.

6. The process of claim 5 wherein said solvent is selected from the group consisting of dimethyl formamide, acetonitrile, acetone, and mixtures thereof.

7. The process of claim 6 wherein said solvent is dimethyl formamide.

8. The process of claim 5 wherein said catalyst is selected from the group consisting of alkali metals, alloys of two or more alkali metals, alkali metal hydrides, alkali metal lower (C1-C4) alkyls, alkaline metal alkoxides of lower ($C_1$-$C_4$) alcohols, carbonates of alkali metals, carbonates of alkaline earth metals, bicarbonates of alkali metals, bicarbonates of alkaline earth metals, and mixtures thereof.

9. The process of claim 8 wherein the catalyst is selected from carbonates of alkali metals, carbonates of alkaline earth metals, bicarbonates of alkali metals and mixtures thereof.

10. The process of claim 8 wherein said catalyst is selected from the group consisting of sodium hydride, lithium hydride, potassium hydride, lithium methoxide, potassium methoxide, sodium methoxide, potassium carbonate, sodium carbonate, barium carbonate, and mixtures thereof.

11. The process of claim 10 wherein said catalyst is potassium carbonate.

12. The process of claim 5, wherein in Step (b) agitation is applied at a Weber Number in the range of from about 5000 to about 15000, and for a period of time in the range of from about 30 minutes to about 6 hours.

13. The process of claim 5 wherein said polyol portion comprises a blend of at least two different polyols.

14. The process of claim 13 wherein said polyol portion comprises sucrose and at least one additional polyol other than sucrose.

15. The process of claim 5 wherein said highly esterified polyol polyester comprises at least two different highly esterified polyol polyesters.

16. The process of claim 15 wherein said highly esterified polyol polyester comprises a highly esterified sucrose polyester and at least one additional highly esterified polyol polyester.

17. The process of claim 16 wherein said polyol portion comprises sucrose and at least one additional polyol other than sucrose.

18. The process of claim 5 wherein in Step (f) isolation of said impurities occurs by a method selected from the group consisting of gravity settling, centrifugation, temperature reduction, and mixtures thereof.

19. The process of claim 18 wherein in Step (f), isolation of said impurities occurs by centrifuging said purified reaction product for a period of time in the range of from about 5 minutes to about 30 minutes, at an applied force in the range of from about 100 G to about 20000 G.

20. The process of claim 19 wherein isolation of said impurities occurs by centrifuging said purified reaction product for a period of time in the range of from about 5 minutes to about 15 minutes, at an applied force in the range of from about 2500 G to about 10000 G.

21. The process of claim 18 wherein said purified reaction product comprises polyol fatty acid polyesters having in excess of about 50% unsaturated fatty acid esters, and wherein in Step (f) isolation of said impurities occurs by centrifuging said purified reaction product for a period of time in the range of from about 5 minutes to about 30 minutes, at an applied force in the range of from about 100 G to about 20000 G.

22. The process of claim 21 wherein isolation of said impurities additionally comprises the step of reducing the temperature of said purified reaction product to a temperature less than about 10 C and removing said impurities.

23. The process of claim 19 wherein in step (g), step (e) and step (f) are repeated for a number of times in the range of from about 1 to about 20 times.

24. The process of claim 23 wherein following step (g), said impurities are further isolated by the process comprising the steps of reducing the temperature of said purified reaction product to a temperature less than about 10 C and removing said impurities after the formation of a discrete impurities layer.

* * * * *